Figure 1:
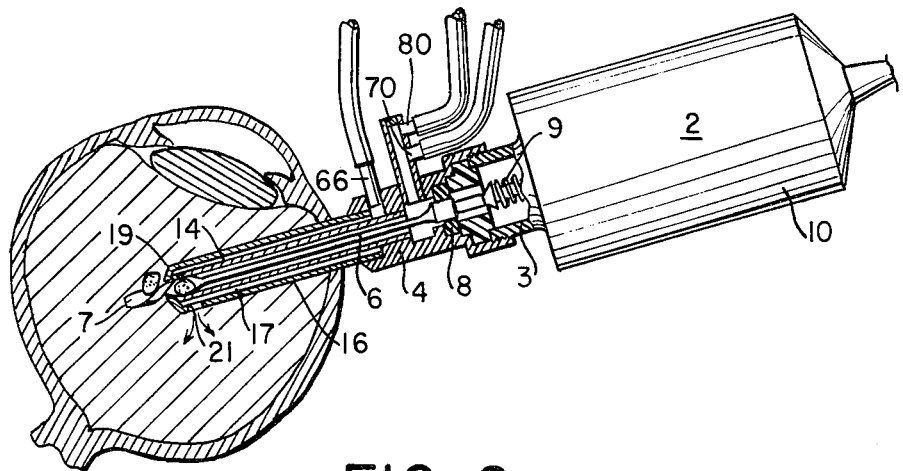

United States Patent [19]

Banko

[11] 4,117,843
[45] Oct. 3, 1978

[54] SURGICAL OPERATING SYSTEM WITH UPPER PRESSURE LIMIT

[75] Inventor: Anton Banko, Bronx, N.Y.

[73] Assignee: Surgical Design Corp., Long Island City, N.Y.

[21] Appl. No.: 796,361

[22] Filed: May 12, 1977

[51] Int. Cl.² ............................................. A61M 1/00
[52] U.S. Cl. ................................... 128/230; 128/305
[58] Field of Search ...................... 128/230, 276, 305; 30/133

[56] References Cited

U.S. PATENT DOCUMENTS

| | | | |
|---|---|---|---|
| 3,906,954 | 9/1975 | Baehr et al. | 128/305 |
| 3,920,014 | 11/1975 | Banko | 128/230 |
| 4,007,742 | 2/1977 | Banko | 128/230 |

Primary Examiner—John D. Yasko
Attorney, Agent, or Firm—Darby & Darby

[57] ABSTRACT

A system for controlling the infusion of fluid to an operating field at a selected predetermined pressure, as a counterpart to an instrument for severing material of an object in the field, and for evacuating through a passage the severed material from the field in a suspension or emulsion of the infusion fluid. The system provides a means for maintaining a constant differential pressure between the operating field and its infusion line and the pressure in the line communicating with the passage through which material is being evacuated at the time a reverse fluid flow mode of operation is initiated in the system to send fluid down the passage through which the severed material is normally evacuated.

11 Claims, 2 Drawing Figures

U.S. Patent    Oct. 3, 1978    4,117,843

SURGICAL OPERATING SYSTEM WITH UPPER PRESSURE LIMIT

RELATED APPLICATIONS

Reference is made to my prior copending application Ser. No. 632,768, entitled SURGICAL SYSTEM FOR CONTROLLING THE INFUSION OF FLUID TO AND THE EVACUATION OF FLUID AND MATERIAL FROM AN OPERATING FIELD, filed Nov. 17, 1975, not U.S. Pat. No. 4,019,514 which application is a continuation-in-part of my prior copending application Ser. No. 475,398, filed June 3, 1974, entitled "Surgical System for Controlling the Infusion of Fluid To And The Evacuation Of Fluid And Material From An Operating Field", now U.S. Pat. No. 3,920,014, granted Nov. 18, 1975 and is also a continuation-in-part of application Ser. No. 632,767, filed Nov. 17, 1975, said application Ser. No. 632,767 also being a continuation-in-part of U.S. Pat. No. 3,920,014. Reference is also made to my issued U.S. Pat. No. 3,812,855 of May 28, 1974, entitled "System for Controlling Fluid and Suction Pressure."

This invention relates to a surgical apparatus and more particularly to an apparatus having particular utility in an operation taking place in a closed operating field, such as the eye of an animal or human being.

In each of my aforesaid prior applications and patents, a system is disclosed for use in conjuction with a surgical instrument of the type which can remove material from an object, such as by cutting, drilling, tearing or by emulsifying, such as by using ultrasonic energy. This system operates to infuse fluid in an operating field for certain purposes, such as to maintain a predetermined pressure, and also for evacuating from the field the severed material removed from the object in suspension with or as an emulsion of the infusion fluid or other fluid present at the operating site.

The systems of the foregoing applictions and patents are capable of performing a variety of functions under the control of an operator. Among these are the supply of infusion fluid to the operating field at a selected predetermined pressure after the surgical instrument is inserted to keep the operating field, for example the eye, formed in its normal shape both before and during the operation. During the operation, the system also operates to: (1) create an evacuation fluid flow in a passage for transporting the material severed by the surgical instrument from the operating field, this material being suspended or emulsified in the supply fluid and in the normal fluid of the operating field; (2) substitute fluid to compensate for the volume of material, both solid and liquid, removed from the operating field; and (3) maintain the pressure in the operating field with workable and safe tolerance levels.

The system also can be operated to generate a reverse flow of fluid through the evacuation fluid flow passage of the instrument when material inadvertently has entered an operative portion of the instrument and has to be moved back into the operating field.

The system of U.S. Pat. No. 3,920,014 also is designed to stop the evacuation of material when the operating mode is terminated by building up the pressurein the evacuation line to approach the level of the pressure in the operating field. This substantially prevents further motion of the material from the operating field into the instrument, thereby preventing the operating field from being emptied of material which would ultimately cause its collapse.

In operating a system of the aforesaid type, during the reverse flow mode, it is desirable to maintain a constant differential pressure between the pressure in the operating field, such as the eye, and the pressure in the evacuation line, which is receiving infusion fluid rather than evacuating, during the time the reverse mode is operating. Heretofore, this has been accomplished, for example, in U.S. Pat. No. 3,920,014 by the use of two separate valves in the line between the pump or compressor which sets the original system pressure and the bottle of fluid which supplies both the infusion fluid and the fluid during the reverse mode.

The present invention is directed to an improved system of the foregoing type in which the pressure differential between the operating and reverse modes can be easily controlled and set at any predetermined differential pressure.

In accordance with the invention, a dual valve is used to set the limits of both the infusion pressure which is used during the operating mode and the reverse pressure. The dual valve is constructed so that when adjusted to cause a change in infusion pressure, a corresponding change is caused in the reverse pressure thereby maintaining a constant differential between the pressure in the operating field and the pressure in the evacuation line at the start of the reverse operating mode of the system.

It is therefore an object of the present invention to provide an improved surgical system for controlling the infusion of fluid into an operating field in the reverse flow mode.

A further object is to provide a novel valve for maintaining a constant differential pressure between the line supplying infusion fluid to the operating field and the line supplying fluid to the evacuation line, during the time the infusion fluid is being supplied to the evacuation line.

Another object is to provide a surgical system for including an operative instrument for removing material from an operating site through an evacuation line and for maintaining a constant pressure differential between the source supplying fluid to the operating site and the source (line) supplying fluid to the evacuation line during the time a fluid is being supplied in a reverse direction through the evacuation line.

Figure 2:
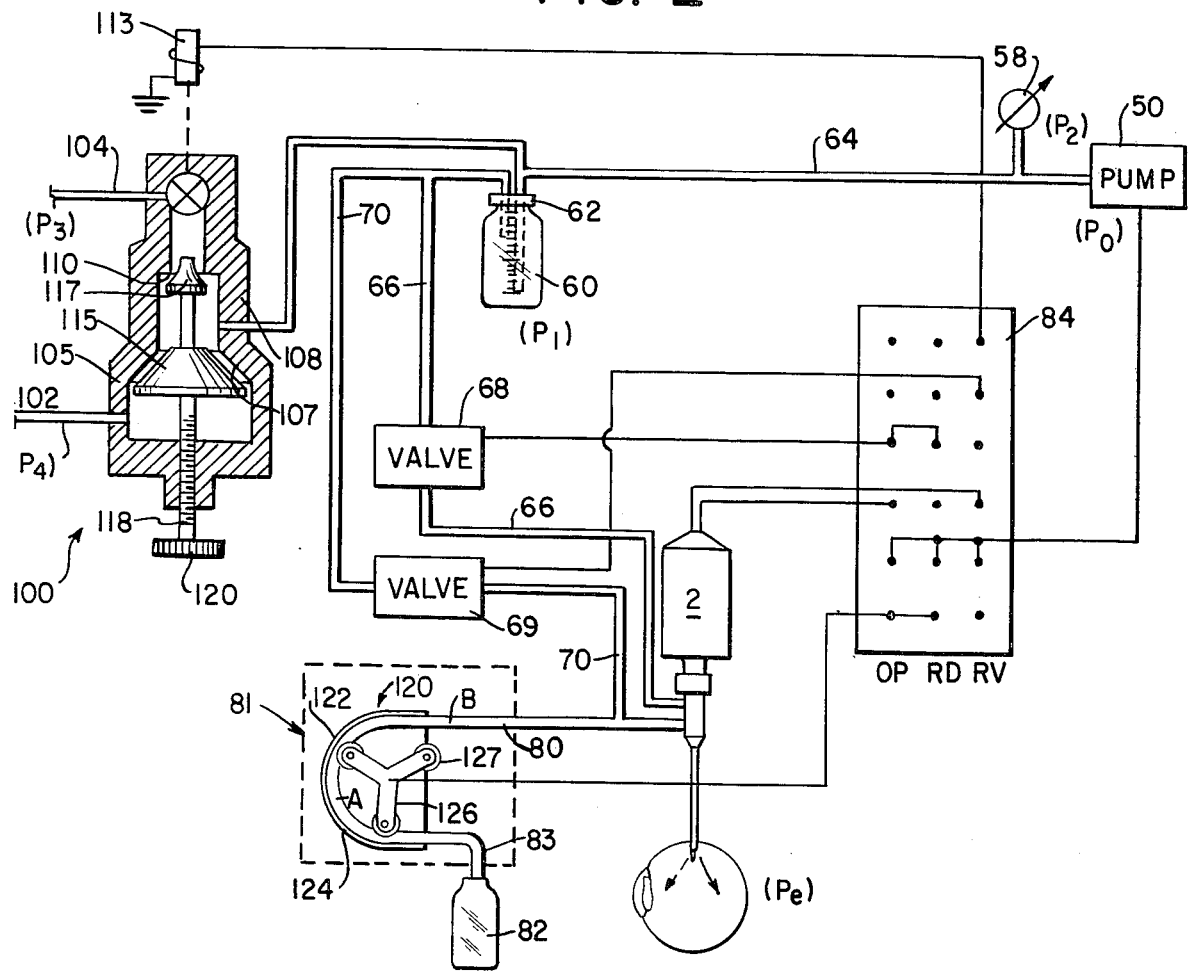

Other objects and advantages of the present invention will become more apparent upon reference to the following specification and annexed drawings, in which:

FIG. 1 is an overall plane view, taken partly in cross-section, of a typical instrument for use with a system of the present invention; and FIG. 2 is a schematic line diagram showing the various components of the system and their operation with particular emphasis on the fluid-flow portions of the system and their various components.

Referring to the drawings, the system is described with respect to performing an operation on the eye of an animal or a human being. It should be understood, of course, that the system can be utilized during the performance of other types of operations and in other environments.

FIG. 1 shows a typical surgical instrument 10 with which the system is used. It should be understood, however, that the system can be used with any type of instrument or instrument set-up which requires pressurized flow of a liquid (infusion) and/or evacuation of fluid and severed material from an operating field. This includes various types of mechanical cutting instruments as well as other instruments, for example those of the ultrasonic type, which act to emulsify material to be removed.

In the embodiment of the invention being described, the tip of instrument 10 is shown as having pierced through a section of the eye, for example, after an incision has been made. The tip of the instrument is shown in the vitreous of the eye to remove tissue therefrom or to treat the eye. The instrument of FIG. 1 also can be used to remove material from other parts of the eye such as the lens or iris. It should be understood that the system can be used with any compatible type of instrument to perform operations or treatment in any portion of the body of a mammal.

The instrument 10 of FIG. 1 includes an electric motor 2, preferably of the reversible type, from which extends a collar 3. A fitting 4 is screwed onto collar 3 and concentric inner and outer tubular members 12 and 16 extend from fitting 4. Inner tube 12 defines a central passage 14 through which evacuation takes place over a line 80, to be described below, which communicates with passage 14 through a coupling on fitting 4. The space between the inner and the outer tubes 12 and 16 defines a passage 17 through which infusion fluid is supplied over a line 66 and reverse flow fluid over a line 70, both of which lines are described below. Lines 66 and 70 communicate with passage 17 through a common coupling in fitting 4.

The inner, evacuation flow, member 14 of the instrument has an opening 19 at the end thereof through which the evacuation flow is applied to the operation field. The infusion flow member 16 has an opening 21 in its wall, spaced from opening 19 to avoid interference. Fluid is injected, or infused into an operating field through opening 21. A shaft 6 having a fluted cutter 7 at the end thereof is located in the inner passage 14. The shaft is connected to the motor output and rotates in bearings 8 in the fitting 4. Shaft 6 is preferably biased by a spring 9 so that the cutter 7 will coact with the surface surrounding the evacuation opening 19 to produce a shearing action to cut any tissue therebetween.

In operation, the tip of the instrument is moved to place the cutter 7 at the site of the material to be severed. The evacuation flow from opening 19 aids in drawing the material into a relationship so that it can be severed by cutter 7. The severed material, in suspension or as part of an emulsion, is drawn up to passage 14 and is removed via passage 14. Infusion fluid is supplied over line 66 to the eye through passage 17 and its opening 21.

FIG. 2 shows the basic fluid flow and electronic control components of a typical system. In these figures, the double lines indicate fluid flow paths and the single lines electrical connections. The infusion fluid supply for the instrument 10 is illustratively shown as a bottle 60 having a calibrated scale thereon. In a typical case, saline solution is utilized as the fluid. Other suitable fluids can be used as needed. The bottle 60 is capped at 62 so that it can be pressurized over a line 64 which extends into the bottle. The line 64 can be of any conventional type of tubing, for example, vinyl or vinyl rubber tubing, and it is connected to a compressor, or pump, 50. Pump 50 is any suitable type producing an air flow over line 64 to pressurize bottle 60. The air entering the infusion bottle 60 is preferably filtered by a suitable filtering means (not shown) to make it sterile.

The pump 50, in conjunction with various regulating valves, produces a constant pressure in line 64 and bottle 60 within selectable, relatively well defined limits, which can be pre-set. This is described below.

An infusion line 66 also extends into the bottle 60 to receive fluid therefrom to be conveyed to the outer passage of the instrument 10. This is the infusion fluid to such passage. Line 66 also can be of vinyl or other suitable material. An electromechanically controlled valve 68 is located in line 66 between bottle 60 and the instrument to control the fluid flow.

A second fluid line 70 also receives fluid from the bottle 60. This is the reverse fluid-flow line whose outlet end is connected to the instrument 10 to supply fluid to the inner passage 16 of the instrument. An electromechanically operated valve 69 is located in line 70 between the bottle 60 and the outlet of reverse flow line 70 to control the flow of infusion fluid to the evacuation passage of the instrument.

An evacuation mechanism 81 removes the severed or emulsified material from the eye through an evacuation line 80 which is connected to the inner passage of the instrument 10. The evacuation is carried out at a substantially constant rate, which can be selected and pre-set, to create a flow of material from the eye in a substantially gasless column of liquid. The evacuation mechanism preferably includes a peristaltic type pump, for example, the Master Flex Tubing Pump, Model 7013 made by Cole-Parmer Company, of Chicago, Illinois. The operation of this type of pump is described in greater detail below. Line 80 empties into a collecting bottle 82 through the pump and a line 83. The material emptied into the bottle 82 includes fluid from the operating field together with the material severed from the object by the instrument.

The system has three modes of operation. The first is the ready made (RD). In the RD mode the system is on, there is infusion fluid flow to the instrument, evacuation flow, but the cutter portion of the instrument is not working. The second mode is the operate (OP) mode where all of the conditions of the ready mode exist and, in addition, the instrument is operating, that is, the cutter is rotating. The third mode is the reverse mode (RV). In the RV mode thee infusion fluid is directed to the evacuation passage of the instrument, there is no evacuation and, if desired, the cutter portion of the instrument is operated in the reverse direction.

The pressure regulation of the system is accomplished in the following manner. The pump 50 produces an output pressure ($P_o$). A variable pressure regulating valve 58 is located in line 64 to set the maximum pressure in the line for all modes of operation. Valve 58, produces a predetermined pressure drop, or leak, of value $P_2$. Valve 58 has a manual control so the drop $P_2$ and the maximum pressure available can be set. In a typical case for operation in the eye, the fluid pressure ($P_2$) it is set at about 120 mm. Hg above the level of fluid in bottle 60. Valve 58 functions during all three modes of system operation.

A second valve 100 is located in line 64. This valve sets the pressures ($P_1$) in the bottle at two different levels through its main bleed outlet 102 and a second leak outlet 104. Valve 100 is of special construction and includes a housing 105 having a conical shaped upper main housing section 107. A cylindrical housing section 1088 extends above section 107. A valve seat 110 is located in the cylindrical section. The leak outlet 104 is controlled by a solenoid 113 which is wired back to switch 84 to open when the switch is in the RD mode. This is described below.

The air pressure inlet to valve 100 from line 64 is over a branch line 60a which enters the valve at a point between two valve members 115 and 117. These two valves 115 and 117 are preferably mounted on a common stem 118 which is threaded into the bottom of housing 105 and is rotatable by a knob 120. If desired, two separate control stems can be used for the two valves 115 and 117. Suitable packings are provided for stem 118 but these are not shown. Valve 115 is of frustro-conical shape on the conical housing section 107 serves as a seat. By rotating stem 118 to move valve 115 upwardly, the air flow from line 60a to bleed outlet 102 becomes more restricted. The outlet pressure of bleed outlet 102, that is the amount of air bled, is designated $P_4$. By moving valve 115 downwardly the amount of air bled out through opening 102 is increased.

Upper valve 117 is of conical shape and acts with seat 110, which is generally ring-shaped, to control the amount of air leaked out of passage 104. The leak pressure is called $P_3$. All or a portion of the periphery of upper valve 117 can be contoured with an arcuate surface, cut in or extending outwardly, to modify the flow characteristics of the valve in a manner set forth below. As valve 117 is moved upwardly, the amount of leakage from passage 104 decreases and vice versa. Valve 117 has a varying cross-section so that more air is blocked more rapidly, $P_3$ decreases more rapidly, as valve 117 moves up in the housing. The leak pressure $P_3$ is generally about 10 to 15 mm of Hg in the case of operating on the eye. The shape of valve 117 is contoured so that a substantially constant amount of leakage is maintained whatever the position of bleed valve 115. Since valve 115 and 117 are mounted on a common stem, a predetermined constant pressure differential is produced by the leak valve 117 when the system is operated in the OP mode, whatever the pressure set by bleed valve 115. The solenoid valve 104 closes the leakage during the RV mode, thus creating a higher pressure.

The various pressures and operating conditions are described below:

$P_0$ = pressure of compressor 50
$P_1$ = pressure in bottle 60
$P_2$ = safety valve 58 leak pressure
$P_3$ = leak valve 117 (passage 104)
$P_4$ = bleed valve 115 (passage 102)
$P_e$ = pressure in the eye During operation of the system, the following pressures are produced and the system operates as described:

$P_{1max} = P_0 = P_2$, that is, valve 58 sets the maximum pressure in bottle 60.

$P_{1_{RD}} = P_0 - (P_2 + P_3 + P_4)$. During the Ready mode, switch 84 controls solenoid 113 to open the leak passage 104 for valve 117. The maximum pressure $P_{1max}$ will be dropped by the sum of the drops of pressures $P_2 + P_3 + P_4$. At At this time the infusion control valve 68 is open so that fluid is flowing in instrument passage 17. The evacuation pump 81 is operating.

$P_{1_{OP}}$ = same as $P_{1_{RD}}$. Here, in addition, the motor of instrument 10 is rotated to provide cutting action.

$P_{1_{RV}} = P_0 - (P_2 + P_4)$. Solenoid 113 is operated to close leak passage 104 for valve 117. Thus, the infusion pressure in the bottle during RV is higher than that during RD by the drop $P_3$. At this time the infusion control valve 68 is closed and the reverse flow valve 69 is open. This sends the infusion fluid down the inner instrument passage 114 where the evacuation flow normally takes place. Evacuation pump 81 is stopped. At this time, the motor of instrument 10 is reversed.

The pressure in the eye ($P_e$) is somewhat less than $P_1$ at any time due to further pressure drops in the system due to resistance to flow. As shown above, valve 100 provides a simple arrangement embodied in a single valve for setting $P_e$ during the RD and OP mode, that is, by setting $P_{1_{RD}}$ and $P_{1_{OP}}$, and for keeping a constant differential between $P_{1_{RD}}$ and $P_{1_{OP}}$ and $P_{1_{RV}}$. Thus, the pressure in the eye will be higher during the RV mode but the increase is kept at a constant difference by the action of valve 117.

What is claimed is:

1. A surgical system comprising:
   first means including a passage for removing material from an operating site,
   second means for infusing a fluid into said operating site,
   third means coupled to said second means for infusing a fluid through said passage of said first means in a direction opposite to that of the flow of material being removed from the operating site,
   said second means including first control means responsive to the operation of the first means for establishing the pressure of the fluid infused into the operating site at a first predetermined pressure when said first means is operating to remove material from the operating site and responsive to the operation of the third means for establishing the pressure of the fluid infused into the operating site by said third means at a second predetermined pressure which is greater than said first predetermined pressure.

2. A surgical system as in claim 1 wherein said first control means comprises valve means, said valve means including first and second valve member, a respective seat for each of said first and second valve members, said valve means also including a respective outlet passage for each of said first and second valve members.

3. A surgical system as in claim 2 further comprising means connecting said first and second valve members for moving them together with respect to their respective valve seats to thereby simultaneously adjust said first and second predetermined pressures.

4. A surgical system as in claim 3 wherein said means connecting said first and second valve members comprises a common stem, means connected to said stem and accessible from outside of the valve means for moving said stem to adjust the position of said first and second valve member relative to their respective seals.

5. A surgical system as in claim 2 wherein said first and second valve members are shaped with respect to each other to maintain a differential between said first and said second predetermined pressures which is a function of the respective shapes.

6. A surgical system as in claim 4 wherein the shapes of said first and second valve members maintain a substantially constant differential between said first and second predetermined pressures.

7. A surgical system as in claim 5 further comprising means connecting said first and second valve members for moving them together with respet to their respective valve seats to thereby simultaneously adjust said first and second predetermined pressures.

8. A surgical system as in claim 7 wherein said means connecting said first and second valve members comprises a common stem, means connected to said stem and accessible from outside of the valve means for moving said stem to adjust the position of said first and second valve member relative to their respective seals.

9. A surgical system as in claim 5 wherein said first valve member is generally conical in shape.

10. A surgical system as in claim 9 wherein said second valve member is also generally conical in shape and the seat for said second valve member is generally ring shaped.

11. A surgical system as in claim 1 further comprising means for selectively opening and closing the outlet passage for said second valve in response to the operation of said third means.

* * * * *